US012655383B2

(12) United States Patent
Rieu et al.

(10) Patent No.: US 12,655,383 B2
(45) Date of Patent: Jun. 16, 2026

(54) EXTRACELLULAR MATRIX SUBSTITUTE IN A CELLULAR MICROCOMPARTMENT

(71) Applicant: TREEFROG THERAPEUTICS, Pessac (FR)

(72) Inventors: Clément Rieu, Bordeaux (FR); Joffrey Mianné, Pessac (FR); Warter Elise, Talence (FR); Maxime Feyeux, Talence (FR)

(73) Assignee: TREEFROG THERAPEUTICS, Pessac (FR)

( * ) Notice: Subject to any disclaimer, the term of this patent is extended or adjusted under 35 U.S.C. 154(b) by 391 days.

(21) Appl. No.: 18/223,164

(22) Filed: Jul. 18, 2023

(65) Prior Publication Data
US 2024/0043793 A1 Feb. 8, 2024

(30) Foreign Application Priority Data
Aug. 8, 2022 (FR) ..................................... 2208170

(51) Int. Cl.
C12N 5/00 (2006.01)
(52) U.S. Cl.
CPC ........ C12N 5/0012 (2013.01); C12N 2513/00 (2013.01); C12N 2533/56 (2013.01); C12N 2533/74 (2013.01)
(58) Field of Classification Search
CPC .................................................. C12N 5/0012
See application file for complete search history.

(56) References Cited

U.S. PATENT DOCUMENTS

| | | | |
|---|---|---|---|
| 9,938,501 B2 * | 4/2018 | Katz ....................... | A61P 19/08 |
| 2012/0142069 A1 | 6/2012 | Shea et al. | |
| 2014/0127290 A1 | 5/2014 | He et al. | |
| 2019/0331662 A1 * | 10/2019 | Ozbolat .............. | C12N 5/0676 |
| 2020/0164109 A1 * | 5/2020 | Kroll ..................... | B33Y 80/00 |

OTHER PUBLICATIONS

Abou-El-Enein, Cytotherapy, 2013, vol. 15, pp. 362-383 (Year: 2013).*
Merriam-Webster online dictionary, 2025, definition of "layer" (Year: 2025).*
Zhou, et al., "The fast release of stem cells from alginate-fibrin microbeads in injectable scaffolds for bone tissue engineering", Biomaterials, Oct. 2011, pp. 1-19, vol. 32, No. 30.
Shikanov, A., et al., "Interpenetrating fibrin-alginate matrices for in vitro ovarian follicle development", Biomaterials. Jun. 29, 2009, pp. 5476-5485, vol. 30, No. 29.
(Continued)

*Primary Examiner* — Mark L Shibuya
(74) *Attorney, Agent, or Firm* — Greer, Burns & Crain, Ltd.

(57) ABSTRACT
A cellular microcompartment comprising: at least one layer of cells, an outer layer of hydrogel, and a fibrin mesh arranged between the outer layer of hydrogel and said layer of cells, the cellular microcompartment being compliant with regulations for Good Manufacturing Practices (GMP) and suitable for clinical applications, as well as methods for preparing the cellular microcompartment, and methods in which the cellular microcompartment is used for production of cells and/or tissues, including a large-scale production.

24 Claims, 6 Drawing Sheets

A = Alginate = Alginate 2%
CS= Suspended cells + culture
medium + Fibrinogen
IS= Intermediate solution = Sorbitol +
Thrombin at 0,02U

CaCl2 Bath

Capsules in suspension in the rinsing medium

Final medium comprising the capsules in suspension

(56)                 References Cited

OTHER PUBLICATIONS

Ikeda, K. et al., "3D culture of mouse iPSCs in hydrogel core-shell microfibers", MEMS, Jan. 18, 2015, p. 463-464.

Alessandri K., et al. "A 3D printed microfluidic device for production of functionalized hydrogel microcapsules for culture and differentiation of human Neuronal Stem Cells (hNSC)", Lab Chip, Apr. 26, 2016, pp. 1593-1604, vol. 16, No. 9.

Kang, S., et al., "Alginate Microencapsulation for Three-Dimensional In Vitro Cell Culture", ACS Biomaterials Science & Engineering, Jul. 12, 2021, pp. 2864-2879, vol. 7, No. 7.

Poorna, MR., "A potential platform for induced pluripotent stem cell culture and differentiation", Colloids and Surfaces B: Biointerfaces, Jul. 18, 2021, pp. 1-13, vol. 207.

* cited by examiner

A = Alginate = Alginate 2%
CS= Suspended cells + culture medium + Fibrinogen
IS= Intermediate solution = Sorbitol + Thrombin at 0,02U

CaCl2 Bath

Capsules in suspension in the rinsing medium

Final medium comprising the capsules in suspension

A = Alginate = Alginate 2%
CS= Suspended cells + culture medium + Fibrinogen
IS= Intermediate solution = Sorbitol CaCl2 Bath
+ Thrombin at 0,02U Capsules in suspension in the rinsing medium Final medium comprising the capsules in suspension Final medium comprising the capsules in suspension + Thrombin at 0,02U

Capsules in suspension in the rinsing medium

A = Alginate = Alginate 2%

CS= Suspended cells + culture medium + Fibrinogen

IS= Intermediate solution = Sorbitol

CaCl2 Bath

EXTRACELLULAR MATRIX SUBSTITUTE IN A CELLULAR MICROCOMPARTMENT

CROSS-REFERENCE TO RELATED APPLICATIONS

This application claims the benefit to priority from French patent application FR 2208170 filed Aug. 8, 2022, the entire disclosure of which is herein incorporated by reference in its entirety.

TECHNICAL FIELD

The invention relates to the field of three-dimensional cell culture and relates, in particular, to cellular microcompartments for the production of cells and tissues capable of being used in GMP clinical conditions for human and veterinary use.

BACKGROUND

Cell culture is a domain which has continued to draw increasing interest since the discovery of induced pluripotent stem cells (iPS or iPSCs) by Prof. Yamanaka.

Historically, cells, including induced pluripotent stem cells, were cultured in two dimensions. Due to the limitations of the two-dimensional cell culture, three-dimensional culture systems have been developed in recent years, making it possible to partially overcome the disadvantages of two-dimensional culture.

Indeed, such systems are advantageously closer to in vivo natural systems, and can be used for numerous applications, in particular in cell therapies. The cells cultured in these systems may be of any type. It may be both differentiated cells with different phenotypes, progenitor cells and stem cells.

A particularly suitable technology is that described in patent application WO 2018/096277, which consists of three-dimensional microcompartments for culturing stem cells.

Although it is a highly promising technology, three-dimensional culture still suffers from certain drawbacks in order to be able to be used in clinical conditions. To do this, both the cells and the three-dimensional culture systems from which the cells come must comply with the regulations relating to Good Manufacturing Practices (GMP). However, most three-dimensional culture systems, such as cellular microcompartments, comprise an extracellular matrix, of animal origin and/or from cancer cell lines, which are incompatible with such regulations.

For cell therapies based on this technology and for production of animal or plant cells for human or animal food consumption, there is therefore a need to develop a substitute for extracellular matrix such that the extracellular matrix is no longer used and yet cells are supplied with a substrate to which they can adhere and on which they can grow.

SUMMARY

The inventors surprisingly discovered that fibrin made it possible to obtain particularly promising results during its use in cellular microcompartments, in that it makes it possible in particular to obtain large quantities of cells, with rapid growth, and also large-scale production of cellular microcompartments. Such results thus make it possible to envisage a clinical applications of three-dimensional cellular microcompartments for human and veterinary use.

To meet this need for cellular microcompartment without any non-GMP extracellular matrix such as Matrigel®, the invention proposes a three-dimensional culture system based on a cellular microcompartment comprising a fibrin mesh arranged between an outer layer of hydrogel and at least one layer of cells.

The invention relates to a new cellular microcompartment comprising:
  at least one layer of cells,
  an outer layer of hydrogel, and
  a fibrin mesh arranged between the outer layer of hydrogel and the at least one layer of cells.

Advantageously, the fibrin mesh may or may not be segregated, that is, entangled with at least one of the other constituents of the cellular microcompartment, such as the cells or the outer layer of hydrogel. Thus, according to one embodiment, the cells can be distributed inside the fibrin mesh and/or the fibrin mesh can be entangled in the outer layer of hydrogel. Preferentially, the fibrin mesh is entangled in the outer layer of hydrogel.

When the fibrin mesh is entangled with the outer layer of hydrogel, the latter can form an interpenetrating network or not. When it forms an interpenetrating network, it may be an interpenetrated polymer network (IPN)

When the fibrin mesh forms a distinct network, it is not entangled with at least one of the other components of the cellular microcompartment.

Advantageously, the fibrin mesh may comprise other molecules, for example growth factors, proteins, peptides, elements of the culture medium and/or derived from cell activity, for example secreted proteins, metabolites, etc.

According to another object, the layer of hydrogel preferentially comprises alginate.

Advantageously, the cells constituting the layer of cells are chosen from eukaryotic cells, pluripotent cells and differentiated cells.

According to another preferred object, the microcompartment according to the invention comprises at least one of the following features:
  The microcompartment is closed, and/or
  the microcompartment is a 3-dimensional microcompartment, preferentially a hollow 3-dimensional microcompartment, and/or
  the microcompartment is in the shape of an ovoid, a cylinder, a spheroid, a sphere or a teardrop, and/or
  the microcompartment comprises one or more lumens within said at least one layer of cells.

When the microcompartment comprises a lumen, the layer of cells, the fibrin mesh and the outer layer are organised around the lumen. Preferably, the layer of cells, the fibrin mesh and the outer layer are successively organised around the lumen.

According to a particularly preferred embodiment, fibrin included in the microcompartment according to the invention is obtained by polymerisation of fibrinogen by thrombin. Advantageously, polymerisation of fibrinogen by thrombin is performed during encapsulation and/or after encapsulation.

According to another aspect, the invention also relates to a set of microcompartments, comprising at least one microcompartment according to the invention.

In the context of the invention, the microcompartment is particularly suitable for a cell therapy protocol. Also, another aspect relates to the microcompartment according to the invention or the set of microcompartments according to the invention for use as a medicament.

Furthermore, the microcompartment according to the invention or the set of microcompartments according to the invention can be obtained by any means known to the person skilled in the art.

According to a particularly preferred aspect, the microcompartment according to the invention can be obtained according to a preparation method described below. Thus, the invention also relates to a preparation method comprising the following steps:

a) mixing cells, optionally previously incubated in a culture medium with a mixture of fibrinogen, b) encapsulating the mixture from step a) in a hydrogel layer, c) culturing the capsules obtained in step b) in a culture medium, d) optionally, culturing the capsules resulting from step c) for at least 1 day, preferentially from 3 to 50 days, and optionally recovering the obtained cellular microcompartments, wherein a thrombin solution is added during step b) and/or c).

Preferably, the method optionally comprises a step for rinsing the capsules resulting from step c), between the culture step c) and the culture step d) for at least 1 day.

Preferably, the encapsulation step b) comprises the following sub-steps:

i. bringing the mixture of step a) into contact with a solution of hydrogel to form at least one drop, and ii. collecting said obtained drop in a calcium bath capable of stiffening the hydrogel solution to form the outer layer of each microcompartment, the inner part of each drop consisting of the mixture of step a) and optionally of the thrombin solution.

More preferably, the thrombin solution can be added during step i) or ii). When the thrombin solution is added during step i), the drop obtained comprises an outer layer and the internal part of each drop consists of the mixture of step a) and the thrombin solution. Preferentially, the mixture of step i) is carried out during the co-injection by means of a microfluidic or millifluidic injector allowing the formation of the drop and the bringing of thrombin into contact, resulting in the polymerisation of fibrinogen into fibrin.

When the thrombin solution is added during step ii), the thrombin solution is present in the calcium bath capable of stiffening the hydrogel solution to form the outer layer of each microcompartment. The thrombin solution then diffuses through the outer layer of hydrogel allowing the polymerisation of fibrinogen into fibrin.

Alternatively, the thrombin solution can be added after the formation of the microcompartment during step c) of culturing the capsules. The culture medium then comprises a thrombin solution, which diffuses through the layer of hydrogel allowing the polymerisation of fibrinogen into fibrin.

According to a particularly preferred embodiment, step i) consists of bringing the mixture of step a), the hydrogel solution, and an intermediate solution comprising said thrombin solution into contact. For the purposes of the invention, the term "intermediate solution" is intended to mean a solution devoid of molecules capable of stiffening the solution of hydrogel, and/or devoid of calcium. According to a particular embodiment, the intermediate solution is an isotonic intermediate solution. The thrombin solution is thus added during the formation of the drop.

Also, in a particularly preferred embodiment, step b), more preferentially sub-step i), is carried out by simultaneous co-injection of the hydrogel solution, of the mixture of step a) and optionally of said intermediate solution; said co-injection is carried out concentrically via a microfluidic or millifluidic injector forming a jet at the injector outlet consisting of the mixture of said solutions, said jet splitting into drops.

In the context of the invention, the thrombin solution cannot be added before the encapsulation step b) corresponding to the formation of the drop.

Preferably, the fibrinogen concentration is between 5 and 30 mg/mL, more preferentially between 10 and 25 mg/m L. Even more preferably, the fibrinogen concentration is between 14 and 20 mg/m L.

Preferably, the thrombin concentration is between 0.001 U/mL and 2 U/mL, more preferentially between 0.01 U/mL and 1 U/mL, between 0.01 U/mL and 0.05 U/mL, between 0.01 U/mL and 0.03 U/mL, even more preferentially 0.02 U/mL.

Preferably, the final opening diameter of the microfluidic injector is between 50 and 800 μm, more preferentially between 50 and 300 μm, even more preferentially between 80 and 240 μm, and the flow rate of each of the solutions is between 0.1 and 1000 mL/h, preferentially between 1 and 500 mL/h, more preferentially between 10 and 150 mL/h. Even more preferably, the opening of the microfluidic injector is 100 μm or 215 μm and the flow rate of each of the solutions is between 23 mL/h and 100 mL/h.

The microcompartment according to the invention is able to be used in a clinical setting. Also, one aspect of the invention relates to the microcompartment or the assembly of microcompartment according to the invention for use as a medicament.

Finally, according to another aspect, the invention also relates to the use of a kit intended for the preparation of a microcompartment according to the invention, said kit comprising at least one fibrinogen solution and a thrombin solution.

According to another aspect, the invention also relates to a kit comprising at least one fibrinogen solution, a thrombin solution, a hydrogel solution, preferentially alginate, an isotonic solution, preferentially a sorbitol solution, a calcium solution, a suitable culture medium. According to a particularly preferred embodiment, said kit is a kit-of-parts.

Preferably, the fibrinogen solution and the thrombin solution are of human origin and are compliant with the regulations relating to Good Manufacturing Practices (GMP).

Other features and advantages will emerge from the detailed description of the invention, examples and figures that follows.

BRIEF DESCRIPTION OF THE FIGURES

FIG. 4A represents capsules in the absence of an exogenous extracellular matrix, FIG. 4B shows capsules obtained in the presence of matrigel, FIG. 4C shows capsules according to the invention according to the embodiment of FIG. 2, and FIG. 4D shows capsules according to the invention according to the embodiment of FIG. 1.

DETAILED DESCRIPTION

Definitions

Figure 1:
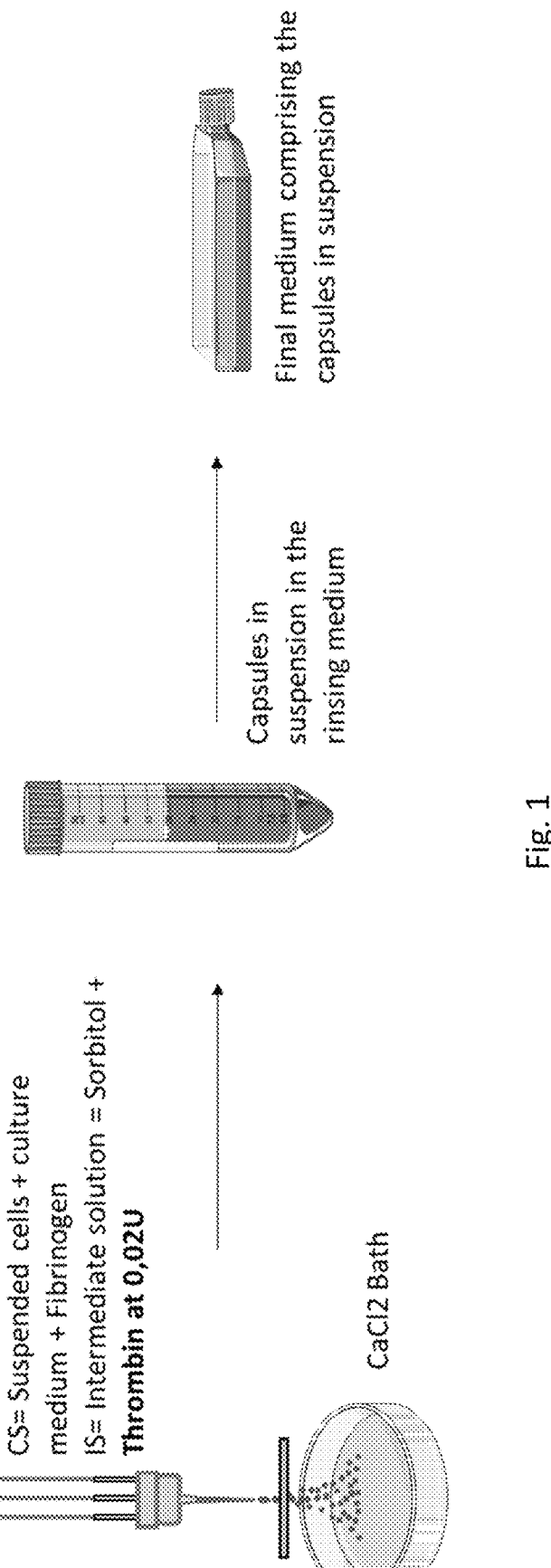
FIG. 1 shows a first embodiment of the invention, during which the thrombin solution is mixed with sorbitol at the time of co-injection. The concentration of the fibrinogen solution is 14 mg/mL. A: 2% alginate, CS: Suspended cells and culture medium and fibrinogen. IS: Intermediate solution comprising sorbitol and thrombin at 0.02 U. The $1^{st}$ step relates to the co-injection of the different constituents forming a jet, splitting into drops in the CaCl2 bath, stiffening the outer layer of the capsule. During the $2^{nd}$ step, the capsules are then resuspended in a rinsing medium. Finally, the capsules are resuspended in a final medium in flasks.

For the purposes of the invention, "microcompartment" or "capsule" also means a partially or entirely closed three-dimensional structure containing a plurality of cells. This is formed from a matrix of polymer chains, for example alginate, inflated by a liquid and preferentially water. The structure consists in particular of a stiffened outer layer of hydrogel.

For the purposes of the invention, "drop" is also understood to mean a three-dimensional structure formed from at least one liquid solution comprising the constituents of a non-stiffened hydrogel (polymerisation precursors, non-crosslinked polymer chains, etc.), of hydrogel precursor elements. Also, the drop constitutes a transient state between the co-injection of the various components and the microcompartment.

For the purposes of the invention, "differentiated" cells means cells which have a particular phenotype, as opposed to pluripotent stem cells which are not differentiated or progenitor cells which are undergoing differentiation.

For the purposes of the invention, "human cells" means human cells or immunologically humanised non-human mammalian cells. Even when this is not specified, the cells, stem cells, progenitor cells and tissues according to the invention consist of or are obtained from human cells or from immunologically humanised non-human mammalian cells.

For the purposes of the invention, the term "mutant cell" refers to a cell carrying at least one mutation.

For the purposes of the invention, "progenitor cell" means a stem cell that is already begun cell differentiation but that has not yet differentiated.

For the purposes of the invention, "embryonic stem cell" means a pluripotent stem cell of cells derived from the internal cell mass of the blastocyst. The pluripotency of the embryonic stem cells can be evaluated by the presence of markers such as the transcription factors OCT4, NANOG and SOX2 and surface markers such as SSEA3/4, Tra-1-60 and Tra-1-81. The embryonic stem cells used in the context of the invention are obtained without destroying the embryo from which they originate, for example using the technique described in Chang et al. (Cell Stem Cell, 2008, 2(2)): 113-117). Optionally, embryonic stem cells from humans can be excluded.

For the purposes of the invention, "pluripotent stem cell" or "pluripotent cell" means a cell which has the capacity to form all the tissues present in the entire organism of origin, without however being able to form an entire organism per se. Human pluripotent stem cells can be called hPSC in the context of the present invention. These may in particular be induced pluripotent stem cells (iPSC or hiPSC for human induced pluripotent stem cells), embryonic stem cells or MUSE cells (for "multilineage-differentiating stress enduring").

For the purposes of the invention, "induced pluripotent stem cell" means a pluripotent stem cell induced to become pluripotent by genetic reprogramming of differentiated somatic cells. These cells are in particular positive for pluripotency markers, such as staining with alkaline phosphatase and expression of the proteins NANOG, SOX2, OCT4 and SSEA3/4. Examples of methods for obtaining induced pluripotent stem cells are described in the articles by Yu et al. (Science 2007, 318 (5858): 1917-1920), Takahashi et al (Cell, 207, 131(5): 861-872) and Nakagawa et al (Nat Biotechnol, 2008, 26(1): 101-106).

For the purposes of the invention, "layer of cells" or "cell seat" is understood to mean a plurality of cells forming a layer or a seat that can be structured around a lumen, it may for example be a cellular tissue or micro-tissue or a three-dimensional grouped culture. The thickness of the layer of cells can be variable. This layer of cells is organised in three dimensions in the microcompartment.

For the purposes of the invention, "tissue" or "biological tissue" has the common meaning for tissue in biology, that is to say, the intermediate organisation level between cell and organ. A tissue is a set of similar cells of the same origin (commonly derived from a common cell line, although they can originate in the association of distinct cell lines), grouped into a cluster, network or bundle (fiber). A tissue forms a functional assembly, that is to say that its cells contribute to the same function. Biological tissues regenerate regularly and are assembled together to form organs.

"Fibrin mesh" or "fibrin network" within the meaning of the invention refers to a plurality of entangled fibrin fibers constituting a mesh or a network.

These are optionally entangled with the inner face of the hydrogel outer layer of the microcompartment.

For the purposes of the invention, "lumen" means a volume of aqueous solution topologically surrounded by cells. Preferably, its content is not in diffusive equilibrium with the volume of convective liquid present outside the microcompartment.

Cellular Microcompartment

The present invention therefore relates to a cellular microcompartment comprising cells, an outer layer of hydrogel and a fibrin mesh. The microcompartment according to the invention comprises at least one layer of cells. It is understood that the microcompartment can also comprise cells in suspension in the medium or optionally housed in the fibrin mesh.

Thus, the cellular microcompartment advantageously comprises:

at least one layer of cells, an outer layer of hydrogel, and a fibrin mesh arranged between the outer layer of hydrogel and said layer of cells.

Preferentially, the microcompartment is a three-dimensional microcompartment, delimited by the outer layer of hydrogel and inside said outer layer, said microcompartment comprises the cells and a fibrin mesh. It may be in the shape of an ovoid, a cylinder, a spheroid, a sphere or a teardrop.

Advantageously, the three-dimensional microcompartment is hollow, more preferentially, the hollow microcompartment is in the form of an ovoid, a cylinder, a spheroid, a sphere or a teardrop.

Preferably, the hydrogel used is biocompatible, that is to say it is non-toxic to the cells. The hydrogel layer must allow the diffusion of oxygen and nutrients in order to supply the cells contained in the microcompartment and to enable them to survive. According to one embodiment, the external hydrogel layer comprises at least alginate. It may consist exclusively of alginate. The alginate can in particular be a sodium alginate, composed of 80% $\alpha$-L-guluronate and 20% $\beta$-D-mannuronate, with an average molecular weight of 100 to 400 kDa and a total concentration of between 0.5 and 5% by weight. Advantageously, the layer of hydrogel is devoid of cells.

The layer of hydrogel also makes it possible to protect the cells from the outside environment, to limit the uncontrolled proliferation of the cells, and their differentiation in case of differentiation.

The cells present in the microcompartment can be any type of cell, in particular the cells are eukaryotic cells, advantageously they are mammalian cells. More preferentially, the cells are human or animal cells.

In a particular embodiment, the microcompartment comprises pluripotent stem cells. A pluripotent stem cell, or pluripotent cell, refers to a cell that has the ability to form all the tissues present in the entire original organism, without being able to form an entire organism as such. The pluripotent stem cells can in particular be induced pluripotent stem cells (iPS), MUSE ("Multilineage-differentiating Stress Enduring") cells that are found in the skin and bone marrow of adult mammals, or embryonic stem cells (ES). According to one embodiment, the microcompartment according to the invention does not comprise embryonic stem cells (ES).

According to a particularly suitable variant of the invention, the microcompartment according to the invention comprises human or animal induced pluripotent stem cells.

In another particular embodiment, the microcompartment according to the invention comprises human or animal multipotent cells and/or human or animal progenitor cells derived from these multipotent cells. The multipotent and/or progenitor cells were preferentially obtained from pluripotent stem cells, in particular human pluripotent stem cells, or optionally from non-pluripotent human cells, the transcriptional profile of which was artificially modified to match that of particular multipotent and/or progenitor cells, typically by forced expression of specific transcription factors for the target cellular phenotype. Preferably, the multipotent and/or progenitor cells were obtained from pluripotent stem cells after bring into contact with a solution capable of initiating the differentiation of said stem cells.

According to another embodiment, the microcompartment according to the invention comprises differentiated human or animal cells. The differentiated cells were preferentially obtained from pluripotent stem cells or from progenitor cells, in particular human pluripotent stem cells or human progenitor cells, or optionally from non-pluripotent human cells, the transcriptional profile of which was artificially modified to match that of particular differentiated cells, typically by forced expression of specific transcription factors for the target cellular phenotype.

Preferably, the differentiated cells were obtained from pluripotent or multipotent or progenitor stem cells after bring into contact with a solution capable of initiating the differentiation of said stem cells. According to one embodiment, the cellular content of the microcompartment comprises homogeneous or mixed cellular identities.

The differentiated cells can in particular be in the form of at least one layer of cells or in the form of a three-dimensional tissue or micro-tissue or in the form of a plurality of tissue or micro-tissues in the microcompartment. It may be a compacted or non-compacted tissue or micro-tissue, with or without a lumen.

The microcompartment according to the invention may comprise a plurality of types of cells. In particular, the microcompartment according to the invention may comprise, for example, stem cells induced to pluripotence and/or multipotent cells and/or progenitor cells and/or differentiated cells.

Advantageously, the microcompartment according to the invention is obtained after a plurality of cell division cycles. Indeed, the cells included in the microcompartment according to the invention are cells obtained by amplification, from at least one cell.

Also, the cells present in the microcompartment according to the invention were obtained after at least two cell division cycles after encapsulation in an outer layer of hydrogel of at least one cell.

Preferably, the cells present in the microcompartment according to the invention were obtained after at least 2, 3, 4, 5, 6, 7, 8, 9, 10, 11, 12, 13, 14, 15, 20, 25, 28, 30 cell division cycles after encapsulation in an outer hydrogel layer of at least 1 cells, preferentially between 1 and 5, between 1 and 10, between 1 and 15, between 1 and 20, between 1 and 30, between 1 and 40, between 1 and 50, between 1 and 60, between 1 and 100 cells. For example, the cells present in the microcompartment were obtained after at least six cell division cycles after encapsulation in an outer layer of hydrogel of at least 1 cell, preferentially between 1 and 50 cells.

Preferably, the microcompartment is obtained after at least 2 passes after encapsulation, more preferentially at least 3, 4, 5, 6, 7, 8, 9 or 10 passes.

Each pass can last for example at least 1 day, or between 2 and 50 days, in particular between 3 and 10 days.

Preferably, the microcompartment is obtained after at least one re-encapsulation, more preferentially between 1 and 14 re-encapsulations, in particular between 2 and 7 re-encapsulations. Very preferentially, a re-encapsulation corresponds to a new passage and each encapsulation cycle corresponds to a pass.

Preferably, all of the cells initially encapsulated in the microcompartment before the first cell division cycle represents a volume less than 50% of the volume of the microcompartment wherein they are encapsulated, more preferentially less than 40%, 30%, 20%, 10% of the volume of the microcompartment wherein they are encapsulated.

Thus, according to one embodiment, the cells present in the microcompartment according to the invention were obtained after at least 2, 3, 4, 5, 6, 7, 8, 9, 10, 11, 12, 13, 14, 15, 20, 25, 28, 30 cell division cycles, after encapsulation in an outer hydrogel layer of cell(s) representing a volume less than 50% of the volume of the microcompartment wherein they are encapsulated, more preferentially less than 40%, 30%, 20%, 10% of the volume of the microcompartment wherein they are encapsulated.

Preferably, in the microcompartment according to the invention, the cells represent more than 50% by volume relative to the volume of the microcompartment, even more preferentially more than 60%, 70%, 75%, 80%, 85%, 90% by volume relative to the volume of the microcompartment.

The microcompartment according to the invention comprises a plurality of cells, preferentially at least 20 cells, even more preferentially at least 100, at least 500, at least 1000, at least 10,000.

In the context of the invention, the fibrin mesh is particularly suitable as substitute for non-GMP extracellular matrices such as Matrigel®, and makes it possible to respond to the disadvantages of the prior art. Also, the fibrin mesh makes it possible to achieve cell multiplication in a satisfactory manner.

Fibrin mesh thus advantageously forms a fibrin network within the capsule, possibly constituting a fibrin gel or clot in the capsule. This mesh may be either interpenetrated with at least one of the other constituents of the microcompartment or not, preferentially with the outer layer of the microcompartment. When the mesh is not interpenetrated, for example with the outer layer, it forms a separate network wherein the cells can be housed and multiply.

Preferably, the fibrin mesh is entangled with the outer layer of hydrogel, more preferentially the inner face of the outer layer of hydrogel. Also, the delimitation between the fibrin mesh and the outer layer may not be perfectly clear. Therefore, at least part of the fibrin mesh can be entangled with the inner face of the outer layer, preferentially with the alginate that composes it. Thus, at least part of the mesh consisting of fibrin is preferentially entangled with the outer layer of hydrogel.

According to another particular embodiment, the fibrin mesh forms an interpenetrated polymer network (IPN) with the outer layer of hydrogel.

According to a particularly preferred object, fibrin is obtained from the polymerisation of fibrinogen by a fibrinogen polymerisation agent, advantageously said agent is thrombin, during encapsulation and/or after encapsulation. Also, the polymerisation of the fibrinogen solution by the thrombin solution takes place during encapsulation and/or afterward. When it takes place after encapsulation, the polymerisation takes place within the newly formed drop or capsule.

The fibrin mesh may optionally comprise a mixture of extracellular proteins and compounds necessary for culturing the cells during differentiation as well as isolated cells.

Advantageously, encapsulation is carried out by means of a co-injection carried out concentrically via a microfluidic injector forming a jet at the injector outlet consisting of the mixture of the various useful solutions, said jet being split into drops. The drops are then collected in a calcium bath capable of stiffening the hydrogel solution to form the outer layer of each microcompartment.

According to a first embodiment, the polymerisation of the fibrinogen solution by thrombin takes place during encapsulation. The mixture of cells, the mixture of fibrinogen, the hydrogel solution and the thrombin solution are simultaneously brought into contact and co-injected concentrically via a microfluidic or millifluidic injector forming the jet at the injector outlet, splitting into drops. As soon as the various solutions are brought into contact, the polymerisation is initiated, this is then carried out almost instantaneously.

According to a second embodiment, the drops are collected in the calcium bath capable of stiffening the hydrogel solution to form the outer layer of each microcompartment. In the absence of thrombin solution during the co-injection via the microfluidic injector, the polymerisation of the fibrinogen is not initiated. Thus, the polymerisation of the fibrinogen solution by the thrombin solution takes place after the encapsulation. According to this object, the thrombin solution is added to the calcium bath allowing the collection and formation of the microcompartment. The thrombin solution can thus diffuse through the hydrogel solution being stiffened.

According to a third embodiment, the thrombin solution is not added into the calcium bath. Therefore, once the process of stiffening the hydrogel solution by the calcium bath has finished, the microcompartments formed are rinsed and an isotonic solution, preferentially a culture medium containing an inhibitor of apoptosis, is added. That isotonic solution is then supplemented with a thrombin solution. The thrombin solution can then diffuse through the stiffened hydrogel shell allowing the polymerisation of fibrinogen by thrombin.

According to a particularly preferred embodiment, the thrombin solution is co-injected simultaneously with the cells, the fibrinogen solution, the culture medium comprising the cells and the hydrogel solution. More preferentially, an isotonic solution is also co-injected and it comprises the thrombin solution, advantageously, the isotonic solution is a sorbitol solution.

According to any of the three embodiments described above, the polymerisation of fibrinogen by a fibrinogen polymerisation agent, such as thrombin, makes it possible to obtain a fibrin mesh within the capsule on wherein the cells will be housed or bound to the surface of the mesh to multiply. The fibrin mesh can either form a distinct network, or form an interpenetrated network with at least one of the other constituents of the microcompartment, preferentially the outer layer of hydrogel.

The microcompartment according to the invention may also comprise other elements, in particular a culture medium.

The culture medium is a medium suitable for the cells present in the microcompartment according to the knowledge of the person skilled in the art.

According to another preferred embodiment of the invention, the microcompartment comprises at least one lumen. The at least one lumen may contain a liquid, in particular the culture medium and/or a liquid secreted by the cells. Advantageously, the presence of this hollow part enables the cells to have a small diffusive volume of which they can control the composition, promoting what is referred to as autocrine/paracrine cell communication. This three-dimensional arrangement in a single layer or spherical cellular seat surrounding the lumen or the central lumen may also be called a cyst.

The lumen is preferentially generated, at the time of the formation of the cyst, by the cells which multiply and develop on or within the fibrin mesh.

According to another preferred object, the layer of cells, the fibrin mesh and the outer layer are organised around the lumen, more preferentially they are organised successively around the lumen.

The conformation in the form of a cyst makes it possible to reduce the pressures experienced by the stem cells relative to the 2D cultures or aggregates. This configuration also makes it possible to reduce cell mortality and to increase the culture amplification factor. Consequently, this makes it possible to reduce the number of passes and dissociations required; to reduce the culture time necessary to reach the necessary number of final cells.

According to one embodiment, the microcompartment may comprise a plurality of cysts or tissues or micro-tissues.

The cellular microcompartment according to the invention is closed or partially closed, that is to say that the outer layer is closed or partially closed. Preferentially, the microcompartment is closed.

The microcompartment according to the invention can be in any three-dimensional form, that is, it may have the shape of any object in space. The microcompartment may have any form compatible with cell encapsulation. Preferentially, the microcompartment according to the invention is in spherical or elongated form. It may have the shape of an ovoid, a cylinder, a spheroid or a sphere. It may in particular be in the shape of a hollow spheroid, a hollow ovoid, a hollow cylinder or a hollow sphere.

It is the outer layer of the microcompartment, that is the hydrogel layer, which imparts its size and shape to the microcompartment according to the invention. Preferentially, the smallest dimension of the microcompartment according to the invention is between 10 μm and 1 mm, preferentially between 100 μm and 700 μm. It may be between 200 μm and 600 μm, in particular between 300 μm and 500 μm.

Its largest dimension is preferentially greater than 10 μm, more preferentially between 10 μm and 1 m, even more preferentially between 10 μm and 50 cm.

The microcompartment according to the invention may optionally be frozen to be stored. It will then have to be thawed before it is used.

The invention also relates to a plurality of microcompartments together.

Thus, the invention also relates to a set or series of cellular microcompartments as described above comprising at least two cellular microcompartments according to the invention.

The invention also relates to an assembly or a series of microcompartments of at least two three-dimensional cellular microcompartments, each microcompartment comprising at least one outer layer of hydrogel and inside said outer layer at least one layer of cells, wherein at least one microcompartment is a microcompartment according to the invention.

Preferably, the cells present in the microcompartments of the set of microcompartments according to the invention were obtained after at least 2, 3, 4, 5, 6, 7, 8, 9, 10, 11, 12, 13, 14, 15, 20, 25, 28, 30 cell division cycles after encapsulation in an outer hydrogel layer of at least 1 cell per microcompartment.

The microcompartment(s) present in this set of microcompartments may have one or more characteristics of a microcompartment according to the invention (size, shape, number of cells, volume of cells, intermediate layer, lumen, etc.).

The set of microcompartments according to the invention preferentially comprises between 2 and $10^{16}$ microcompartment.

Preferably, the series of microcompartments according to the invention is in a culture medium, in particular in an at least partially convective culture medium.

According to a particularly suitable embodiment, the object of the invention is a series of cellular microcompartments in a closed chamber, such as a bioreactor, preferentially in a culture medium in a closed chamber, such as a bioreactor.

The presence of an outer layer of hydrogel and potentially an intermediate layer of isotonic aqueous solution enables uniform distribution of the cells between the microcompartments. Moreover, this hydrogel layer makes it possible to prevent microcompartments from fusing, these fusion events being a major source of variability which is unfavorable for phenotypic homogeneity of the cells.

Method

The microcompartment can be obtained by any means known to the person skilled in the art to prepare microcompartments or capsules.

According to another aspect, the invention also relates to a method for preparing microcompartments according to the invention.

The method for preparing a microcompartment or a set of microcompartments according to the invention comprises at least the following steps:
   a. mixing cells, optionally previously incubated in a culture medium with a mixture of fibrinogen,
   b. encapsulating the mixture from step (a) in a hydrogel layer;
   c. culturing the capsules obtained in step (b) in a culture medium,
   d. optionally, culturing the capsules resulting from step (c) for at least 1 day, preferentially from 3 to 50 days, and optionally recovering the obtained cellular microcompartments,
   wherein a thrombin solution is added during step b) and/or c).

Advantageously, the method according to the invention may comprise additional steps. Thus, preferentially, the cells are incubated prior to the step of mixing the cells with the mixture of fibrinogen in a suitable culture medium. Said culture medium preferentially comprises at least one cyto-protective factor, more preferentially at least one inhibitor of apoptosis.

The inhibitor of apoptosis can for example be one or more inhibitor(s) of RHO/ROCK (Rho-associated protein kinase) pathways, or any other inhibitor of apoptosis known to the person skilled in the art. The inhibitor of apoptosis must make it possible to promote cell survival, the adhesion of the cells to fibrin during the formation of the outer hydrogel layer.

The method according to the invention may comprise a step of dissociation of the cells by chemical, enzymatic or mechanical dissociation, prior to or simultaneously implemented in the cell incubation step, itself carried out prior to step a) of mixing. This step is particularly important in the case of adherent cells.

The encapsulated cells are suspended in the form of single cells and/or cell clusters. Preferably, the single cells represent less than 50% by number of the totality of the encapsulated cells, more preferentially the single cells are hPSC cells. Indeed, it is preferable to encapsulate clusters of cells because this reduces the appearance of the mutagenesis phenomenon.

Preferentially, the steps subsequent to the encapsulation are carried out under permanent or sequential stirring. This stirring is important because it maintains the homogeneity of the culture environment and prevents the formation of any diffusive gradient. For example, it allows homogeneous control of cellular oxygenation level; thus avoiding hypoxia-related necrosis phenomena, or oxidative stress related to hyperoxia. Therefore, it avoids an increase in cell mortality and/or oxidative stress.

Preferentially, after the step of culturing the obtained capsules, the method comprises a step which consists of rinsing the capsules resulting from step (d), advantageously so as to eliminate the cytoprotective factor, such as the inhibitor of apoptosis.

Preferentially, the encapsulation step b) comprises the following sub-steps:

i. bringing the mixture of step a), that is the cells and the mixture of fibrinogen, into contact with a solution of hydrogel to form at least one drop, and ii. collecting said at least one obtained drop in a calcium bath capable of stiffening the hydrogel solution to form the outer layer of each microcompartment, the inner part of each drop consisting of the mixture of step i).

Once the outer hydrogel layer has been stiffened by the calcium bath, the microcompartment is formed. The micro-compartment can then be rinsed, in order to eliminate, for example, the inhibitor of apoptosis.

When the thrombin solution is added during the encapsulation step b), it can be added during step i) of mixing or ii) collecting the drop.

According to one object of the invention, the thrombin solution is mixed with the mixture of step a), and the hydrogel solution, preferentially thrombin is co-injected simultaneously with the other solutions. Preferentially, step i) consists in bringing the mixture of step a), the hydrogel solution, and an isotonic intermediate solution comprising said thrombin solution into contact, more preferentially the isotonic intermediate solution is a sorbitol solution.

Particularly advantageously, the step of mixing the mixture of step a) and the hydrogel is a step which aims to structure in the form of a linear and concentric flow said mixture of step a) and the hydrogel solution.

Advantageously, the addition of thrombin during simultaneous co-injection makes it possible to control the polymerisation in that the thrombin/fibrinogen contact time can be controlled. On the other hand, the amount of thrombin added is less significant, preferentially by a factor of 4 to 8, compared to the addition of the thrombin solution after the encapsulation.

According to another object of the invention, the thrombin solution is added to the calcium bath, that is during step ii). The thrombin solution can thus diffuse through the hydrogel shell of the microcompartment during stiffening and thus polymerise fibrinogen into fibrin. A fibrin mesh is thus formed on or wherein the cells multiply and form a cyst.

When, the method according to the invention comprises a step of rinsing the capsules obtained, the solution constituting the calcium bath is removed and replaced by a suitable medium for culturing the microcompartments according to the invention, preferentially an isotonic solution, more preferentially a culture medium containing an inhibitor of apoptosis. This medium may, according to another object, comprise a thrombin solution. Here again, the thrombin solution can diffuse through the hydrogel shell of the stiffened microcompartment and polymerise the fibrinogen into fibrin, constituting the fibrin mesh. Also, according to another object of the invention, the thrombin solution is added during step c).

Also, in a particularly preferred manner, step b) of the method according to the invention is carried out by simultaneous co-injection of the hydrogel solution, of the mixture of step a) and optionally of said intermediate solution; said co-injection is carried out concentrically via a microfluidic or millifluidic injector forming a jet at the injector outlet consisting of the mixture of said solutions, said jet splitting into drops.

When the thrombin solution is co-injected with the other solutions, it is preferentially mixed with the isotonic intermediate solution.

Preferentially, the fibrinogen concentration is between 5 and 30 mg/mL, preferentially 10-25 mg/mL, more preferentially between 14 and 20 mg/mL.

According to another object of the invention, the concentration of the thrombin is preferentially between 0.001 U/mL and 2 U/mL, more preferentially between 0.01 U/mL and 1 U/mL, between 0.01 U/mL and 0.05 U/mL, between 0.01 U/mL and 0.03 U/mL, even more preferentially 0.02 U/mL. "U" is understood to mean an enzymatic activity unit (that is the concentration for an enzyme) which represents the amount of enzyme necessary to treat a micromole of substrate in 1 minute. It is understood that the indicated concentration is the one in the mixture. Indeed, advantageously thrombin is mixed with the other constituents according to a 1:1 ratio. Also, within the capsule, when the concentration of thrombin, before mixing, is 0.01 U/mL, the concentration in the capsule is about 0.01 U/mL.

The method according to the invention is implemented via a microfluidic injector allowing the co-injection of the various solutions and allowing the formation of a jet splitting into drops. Preferentially, the final opening diameter of the microfluidic injector is between 50 and 800 μm, more preferentially between 50 and 300 μm, even more preferentially between 80 and 240 μm, and the flow rate of each of the solutions is between 0.1 and 1000 mL/h, preferentially between 1 and 500 mL/h, more preferentially between 10 and 150 m L/h.

The method according to the invention is preferentially implemented of a closed chamber such as a closed bioreactor or a flange.

The number of cell divisions in step (d) of culturing the capsules is at least 2, 3, 4, 5, 6, 7, 8, 9, 10, 11, 12, 13, 14, 15 cell division cycles.

Preferentially, the microcompartment is obtained after at least 2 passes (a pass corresponds to a complete cycle of steps (a), (b), and (c), optionally (c), more preferentially at least 3, 4, 5, 6, 7, 8, 9 or 10 passes. Each pass can last for example between 2 and 15 days, in particular between 3 and 8 days.

In a preferred variant, the method according to the invention comprises at least one re-encapsulation of the cells after step (d), that is at least two encapsulation cycles. Preferentially, each encapsulation cycle corresponds to a pass. In this variant of the method (at least one reencapsulation of the cells after step (d) the number of cell divisions of the entire method (for all passes) is at least 3, 4, 5, 6, 7, 8, 9, 10, 11, 12, 13, 14, 15, 20, 25, 30 cell division cycles.

In a method according to the invention, there may be a plurality of re-encapsulations, preferentially between 1 and 100, in particular between 1 and 10 re-encapsulations.

Each re-encapsulation may comprise:

a step which consists in dissociating the microcompartment or the series of microcompartments in order to obtain a suspension of cells or a suspension of cell clusters; the outer layer of hydrogel can be eliminated in particular by hydrolysis, dissolution, piercing and/or breaking by any biocompatible means, that is to say means which are not toxic for the cells. For example, the elimination may be accomplished using phosphate-buffered saline, a divalent ion chelator, an enzyme such as alginate lyase if the hydrogel comprises alginate, and/or laser microdissection, and a step of re-encapsulating all or part of the cells or cell clusters in a hydrogel capsule.

Reencapsulation is a means suitable for increasing the cell amplification obtained from the pluripotent step, and reducing the risks of mutation.

According to a particular embodiment, the re-encapsulation comprises the following steps:

eliminating the outer layer of hydrogel, resuspending the cells that were contained in the microcompartment so as to obtain single cells and/or at least one set or cluster of cells in an isotonic medium, preferentially a culture medium containing an inhibitor of apoptosis, encapsulating the mixture in a hydrogel layer;

preferentially, culturing the microcompartments obtained in an isotonic solution containing an inhibitor of apoptosis, preferentially a culture medium containing an inhibitor of apoptosis;

preferentially, rinsing the microcompartments, advantageously, so as to eliminate the inhibitor of apoptosis;

culturing the microcompartments in an isotonic solution, preferentially a culture medium, for at least one cell division cycle, and optionally recovering the obtained cellular microcompartments.

Methods of Use

The use of a fibrinogen solution and a thrombin solution making it possible to form fibrin as substitute for the extracellular matrix, in particular Matrigel®, is particularly suitable for three-dimensional cell culture, whether the cell culture is implemented by means of cellular microcompartments, tubes or fibers comprising the cells.

Thus, the invention also relates to the use of a kit intended for three-dimensional cultivation, said kit comprising a fibrinogen solution and a thrombin solution. Thus, the invention also relates to a kit comprising a fibrinogen solution and a thrombin solution, wherein the kit is useful for three-dimensional cultivation of cells.

When the kit is intended to be implemented in tubes or fibers comprising the cells, the preparation method can be as follows:

a. mixing cells, optionally previously incubated in a culture medium with a mixture of fibrinogen, b. coating the mixture from step (a) in a hydrogel layer;

c. culturing the fibers or tubes obtained in step (b) in a culture medium, wherein the thrombin solution is added during step b) and/or c).

Advantageously, the coating step b) is implemented by means of a concentric flow. The concentric flow comprising:

a central flow (i) comprising the mixture of cells and fibrinogen of step a), optionally an intermediate flow (ii) positioned further outward from the central flow devoid of calcium and comprising an isotonic solution, for example an isotonic sorbitol solution which can optionally comprise fibrinogen, an outermost flow (iii) relative to the intermediate flow comprising a solution of hydrogel, for example an alginate solution, optionally comprising thrombin, and even further outward, a calcium-free flow (iv) comprising an isotonic solution, for example an isotonic sorbitol solution which may optionally comprise fibrinogen.

According to another aspect, the invention relates to the use of a kit intended for the preparation of a microcompartment according to the invention, said kit comprising a fibrinogen solution and a thrombin solution.

Preferentially, the fibrinogen solution and the thrombin solution are of human origin and are in accordance with the regulations relating to Good Manufacturing Practices (GMP).

Finally, the microcompartment is particularly suitable for use in a clinical setting. Also, the invention also relates to a microcompartment according to the invention or set of microcompartments according to the invention for use as a medicament.

According to another aspect, the invention relates to the use of the microcompartment according to one of the preceding objects, for the production of cells, tissues, preferentially for the large-scale production of such cells and/or tissues.

The microcompartment according to the invention can also be used for the production of animal or plant cells for human or animal food consumption. This use is particularly useful for creating substitutes for meat products such as meat, in order to limit the consumption of meat products.

According to another aspect, the invention also relates to a kit comprising at least one fibrinogen solution, a thrombin solution, a hydrogel solution, preferentially alginate, an isotonic solution, preferentially a sorbitol solution, a calcium solution, a suitable culture medium. According to one variant, said kit is a kit-of-parts.

The invention is now illustrated by non-limiting examples of compositions according to the invention and by results.

EXAMPLES

Example 1—Capsule According to a First Embodiment

This example describes a first embodiment of the invention, also shown in FIG. 1, wherein the thrombin solution is added to the sorbitol solution and co-injected via the microfluidic injector with the mixture of cells in the culture medium and with the hydrogel solution.

Thus, the cells were mixed with cell culture medium and fibrinogen at 14 mg/mL. The microfluidic injector enabling the co-injection of the various solutions comprises three lines upstream of the nozzle. This solution comprising fibrinogen was injected into the line corresponding to the cells and the encapsulation was carried out. The other two lines respectively comprising a 2% alginate solution, and an intermediate solution comprising the sorbitol solution and the thrombin solution at 0.02 U/mL.

Once the encapsulation has been carried out, the drops are collected in the CaCl2 bath allowing the stiffening of the alginate and the formation of the alginate shell forming the microcompartment or capsule. This solution comprising the capsules was then rinsed with a cell culture medium free of serum.

Example 2—Capsule According to a Second Embodiment

Figure 2:
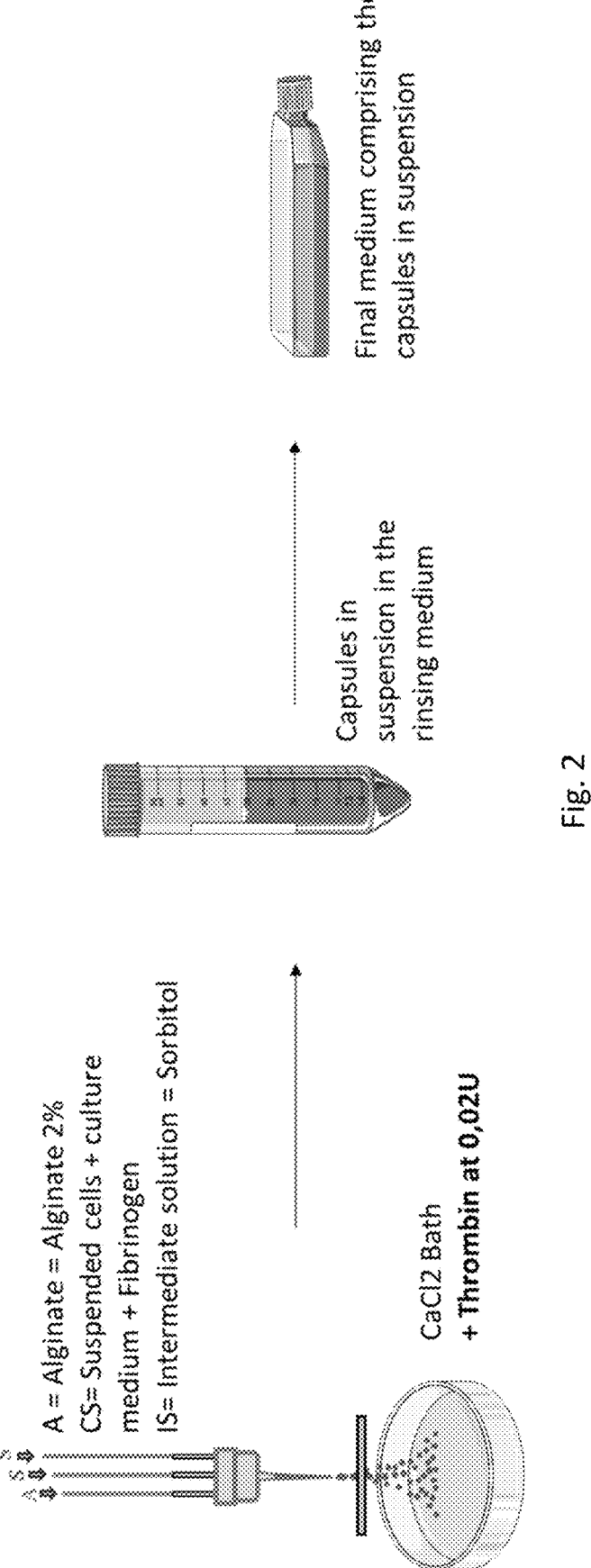
FIG. 2 shows a second embodiment of the invention, during which the thrombin solution is added to the calcium bath, used to collect the drops forming after the splitting of the jet at the injector outlet. The concentration of the fibrinogen solution is 14 mg/mL. A: 2% alginate, CS: Suspended cells and culture medium and fibrinogen. IS: Intermediate Solution, namely sorbitol. The 1$^{st}$ step relates to the co-injection of the various constituents forming a jet, splitting into drops in the $CaCl_2$ bath supplemented with the thrombin solution at 0.02 U, allowing the polymerisation of fibrinogen and the stiffening of the outer layer of the capsule, consisting of alginate. During the 2$^{nd}$ step, the capsules are then resuspended in a rinsing medium. Finally, the capsules are resuspended in a final medium in flasks.

This example describes a second embodiment of the invention, also shown in FIG. 2, wherein the thrombin solution is added into the calcium bath, wherein the drop newly formed after the fragmentation of the jet at the outlet of the microfluidic injector will be collected.

The cells were mixed with cell culture medium and fibrinogen at 14 mg/mL, this solution was injected into the corresponding line upstream of the microfluidic injector and the encapsulation was carried out. The other two lines respectively comprising a 2% alginate solution, and an intermediate solution comprising the sorbitol solution.

Once the encapsulation has been carried out, the capsules are collected in the solution constituting the CaCl2 bath and supplemented with the solution of Thrombin at 0.02 U. This solution was rinsed with a serum-free cell culture medium.

Example 3—Capsule According to a Second Embodiment

Figure 3:
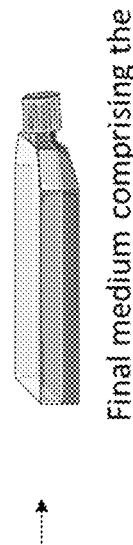
FIG. 3 shows a first embodiment of the invention, during which the thrombin solution is added to the final culture medium. The concentration of the fibrinogen solution is 14 mg/mL. A: 2% alginate, CS: Suspended cells and culture medium and fibrinogen. IS: Intermediate Solution, namely sorbitol. The first step relates to the co-injection of the different constituents forming a jet, splitting into drops in the $CaCl_2$ bath, stiffening the outer layer of the capsule, consisting of alginate. During the 2$^{nd}$ step, the capsules are then resuspended in a rinsing medium. Finally, the capsules are resuspended in a final medium supplemented with the thrombin solution at 0.02 U in flasks, allowing the polymerisation of fibrinogen.
Figure 3:
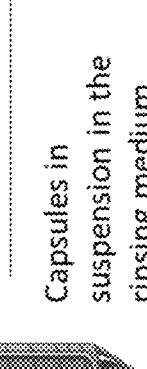
Figure 3:
Figure 3:
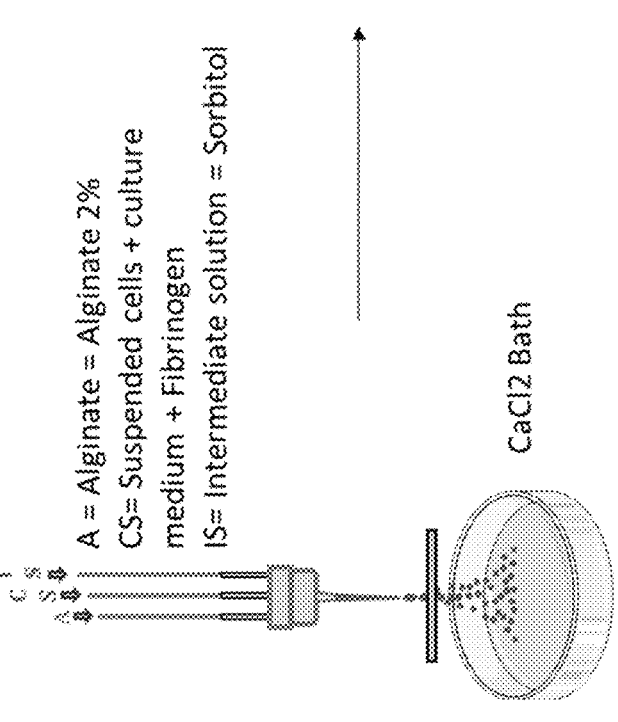
Figure 4:
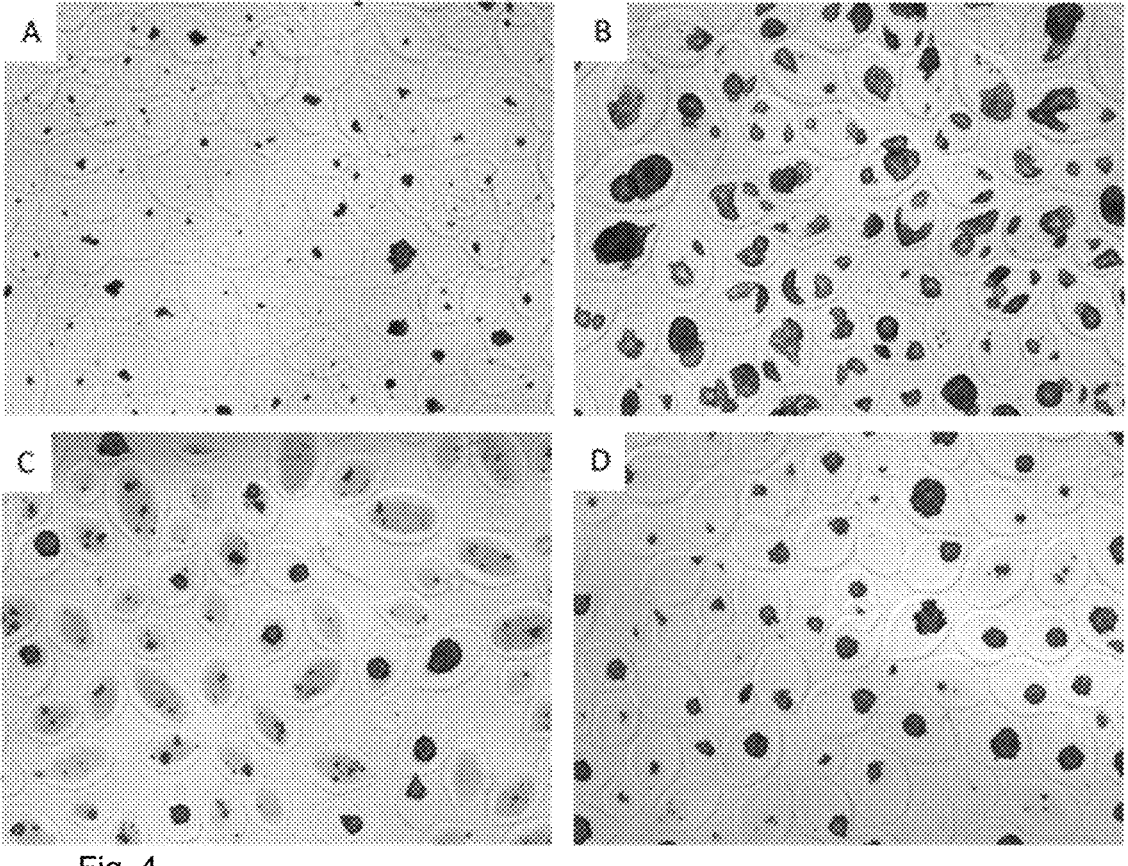
FIG. 4A-4D are a phase contrast microscopy image at D5 as follows.

This example describes a third embodiment of the invention, also shown in FIG. 3, wherein the thrombin solution is added into an isotonic solution after rinsing the capsules obtained after the stiffening of the alginate by the action of the calcium bath.

The cells were mixed with cell culture medium and fibrinogen at 14 mg/mL, this solution was injected into the corresponding line upstream of the microfluidic injector and the encapsulation was carried out. The other two lines respectively comprising a 2% alginate solution, and an intermediate solution comprising the sorbitol solution.

Once the encapsulation has been carried out, the capsules are collected in the solution constituting the CaCl2 bath and this solution was rinsed with a serum-free cell culture medium and supplemented with the Thrombin solution at 0.02 U.

Example 4—Comparative Results of the Capsules According to the Invention and Matrigel®-Based Capsules Comparative results were carried out between microcompartments of the prior art in the presence of extracellular matrix, in particular Matrigel®, or in the absence of an exogenous extracellular matrix or extracellular matrix substitute, compared to the microcompartments according to the invention. Although Matrigel® represents the most efficient solution to obtain cysts, it is not suitable for the use of clinical capsules, for example in the context of differentiated cell production. By way of example, the capsules can produce a large number of neuronal cells that can be injected into patients with neurodegenerative diseases, for example Alzheimer's disease. Thus, the product directly obtained by the capsules according to the invention can be used in the context of cell therapy. The capsules and the cells obtained thus need to comply with GMP regulations. However, Matrigel®, given its composition, cannot be used under GMP conditions. This problem is satisfactorily solved with the fibrin mesh as shown in the results below.

Protocol

In the context of this test, the inventors used an iPS cell line that was generated according to the usual standards of two-dimensional iPS culture, then the cells were detached from the flasks via the action of an enzyme, according to the knowledge of the person skilled in the art and transferred to the culture medium suitable for the culture of iPS.

The iPS cells were mixed in a suitable culture medium, comprising a solution of fibrinogen at 14 mg/mL, so as to obtain a cell density of the order of 3 M/mL. The thrombin solution was mixed in a sorbitol solution. The various solutions were then loaded via the dedicated lines and co-injected simultaneously by means of a microfluidic injector. The amount of cells encapsulated is on the order of 1.21 CM.

The same protocol was implemented in order to obtain capsules free of an exogenous extracellular matrix and capsules with Matrigel®.

From D1 to D5 after encapsulation, the capsules are visually checked. On D5, the appearance of the cells, the amount of cells, their viability and pluripotence are observed.

Results

The results presented in FIG. 4A-4D, FIG. 5, FIG. 6, and FIG. 7.

FIG. 4A-4D shows capsules free of exogenous extracellular matrix (A), capsules comprising Matrigel® (B), capsules according to the invention according to example 2 (C), and capsules according to the invention according to example 1 (D). Phase contrast microscopy images were generated and the inventors observed the obtaining of capsules comprising at least one layer of cells, an outer layer of hydrogel and a fibrin mesh (C) and (D) in comparison with the capsules of the prior art based on Matrigel® (B), and capsules without an exogenous extracellular matrix (A).

Figure 5:
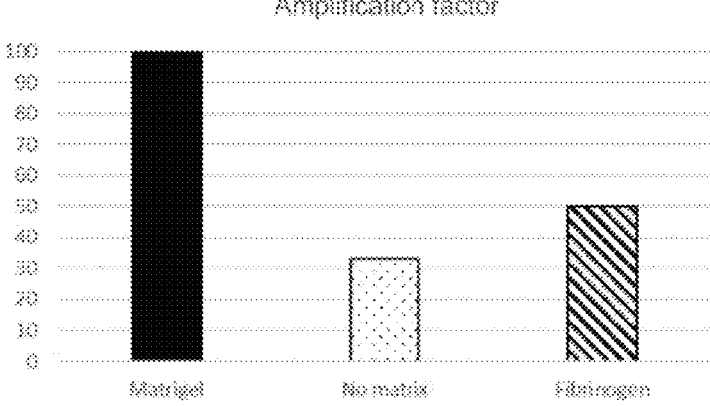
FIG. 5 shows the results relating to the amplification of the capsules according to the invention, capsules in the presence of matrigel, and capsules in the absence of an exogenous extracellular matrix.

The inventors then characterised the capsules obtained. The results in FIG. 5 show the results relating to the amplification of the capsules according to the invention, capsules in the presence of Matrigel®, and capsules in the absence of an exogenous extracellular matrix. The inventors observed better amplification with fibrin compared to the absence of exogenous but lower extracellular matrix compared to Matrigel®. However, the results obtained demonstrate that the fibrin mesh-based capsules allow good amplification of the capsules allowing their use to produce cells.

Figure 6:
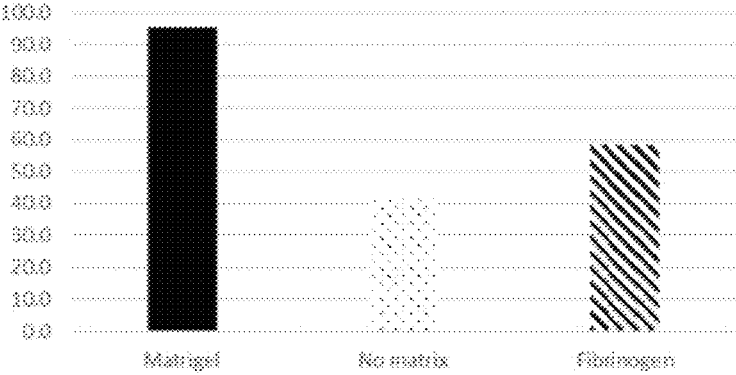
FIG. 6 shows the results relative to the percentage of capsules comprising a cyst for the capsules according to the invention, the capsules in the presence of matrigel and the capsules free of an exogenous extracellular matrix.

The results in FIG. 6 represent the percentage of capsules comprising a cyst, whether for the capsules according to the invention, the capsules in the presence of Matrigel® and the capsules free of an exogenous extracellular matrix. The inventors observed the presence of at least one cyst in about 60% of the capsules according to the invention. Here again, the results obtained demonstrate that the fibrin mesh-based capsules make it possible to obtain a cyst and therefore their uses to produce cells.

Figure 7:
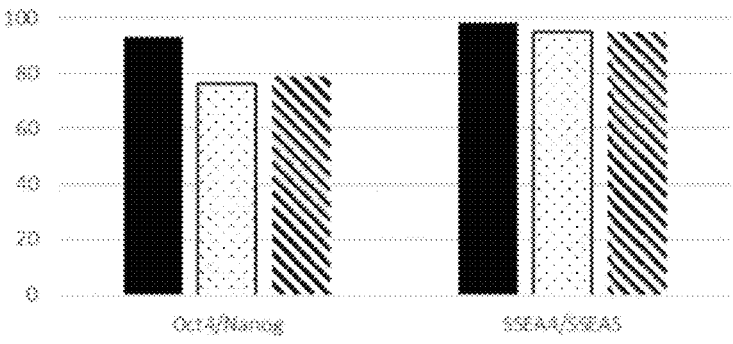
FIG. 7 shows the results relating to pluripotence for capsules according to the invention, capsules in the presence of matrigel, and capsules in the absence of an exogenous extracellular matrix.

The results in FIG. 7 show the results relating to pluripotence for capsules according to the invention, capsules in the presence of Matrigel®, and capsules in the absence of an exogenous extracellular matrix. In this test, the inventors observed more cells positive for Oct 4, Nanog, SSEA4 and SSEA5 (characteristic factors of the iPS cells) in the capsules comprising fibrin than those free of an exogenous extracellular matrix, thus demonstrating that the fibrin-based capsules make it possible to maintain the pluripotence of the cells and therefore their viability.

The results thus demonstrate that fibrin is present as a satisfactory extracellular matrix substitute in the context of the invention, although exhibiting results slightly below Matrigel®. Indeed, fibrin is systematically greater than the use of a capsule free of an exogenous extracellular matrix and makes it possible to obtain good amplification, to maintain pluripotence, and to develop cysts, in a satisfactory manner.

Thus, the use of fibrin, in particular the use of a fibrin mesh makes it possible to overcome the disadvantages of the prior art allowing the use of this three-dimensional microcompartment technology based on fibrin mesh, in a clinical setting in the context of cell therapies.

Example 5—Capsule According to the Invention in the Context of a Protocol for Differentiating iPS Cells into Neural Tissue This study aims to use the microcompartment according to the invention in the context of a protocol for differentiating PS cells into neural tissue.

Protocol

Once the cellular microcompartments according to the invention have been obtained comprising iPS cells, they will undergo cell differentiation so as to differentiate them into neural cells according to the desired phenotype.

In the context of this test, the method implemented is adapted from Kriks et al. ("Dopamine neurons derived from human ES cells efficiently engraft in animal models of Parkinson's disease", Nature 2011 Nov. 6; 480(7378): 547-51) and from Nolbrant et al. ("Generation of high-purity human ventral midbrain dopaminergic progenitors for in vitro maturation and intracerebral transplantation", Nature Protocols 2017).

Capsules comprising iPS cells, then differentiated into neural tissue, are cultured for 24 days after encapsulation.

Results

Figure 8:
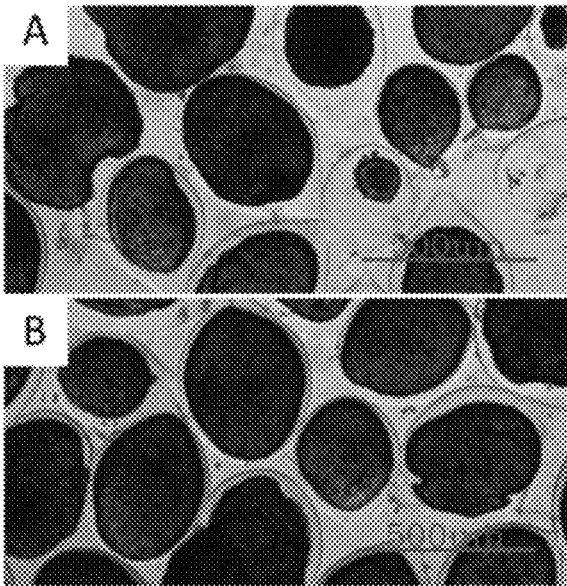
FIG. 8 is a phase contrast microscopy image at D17 post-encapsulation, of neurons. Panel A represents neurospheres or neural microtissue comprised in the microcompartments according to the invention, namely polymerised fibrin from fibrinogen at 14 mg/mL, and panel B of neurospheres or neural microtissue in prior art microcompartments comprising matrigel.
Figure 9:
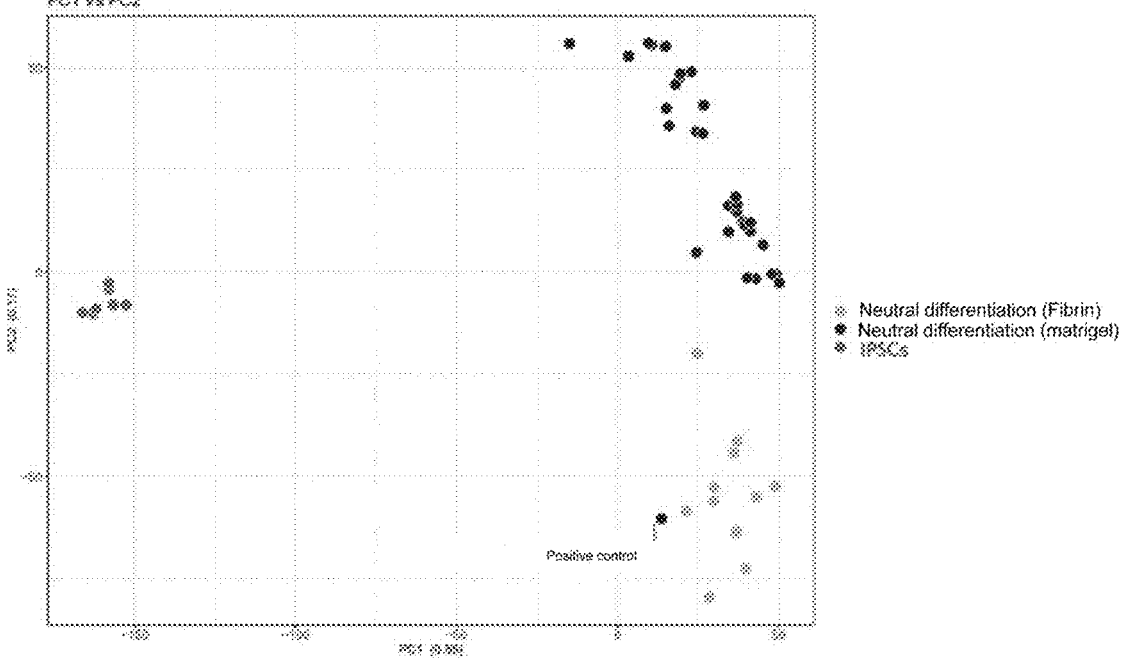
FIG. 9 shows a principal component analysis (PCA) of the 1000 most variable genes between the iPSCs at d0 and at d17, d24 after neural differentiation in capsules inoculated with fibrinogen or matrigel. The matured dopaminergic progenitors in capsules are used as a positive control.

The results are presented in FIG. 8 and FIG. 9. The inventors thus observed the presence of neural tissue 24 days after encapsulation from iPS cells. Panel A is an image representing the microcompartments according to the invention based on polymerised fibrin from fibrinogen at 14 mg/mL, and panel B represents microcompartments of the prior art based on Matrigel®.

The inventors were thus able to observe the presence of neural tissue, in particular neurospheres having a similar size whether in fibrin-based capsules or Matrigel®-based capsules. The neural tissue at D24 indeed expresses tyrosine hydroxylase (TH), a specific marker of neuronal cells constituting neural tissue.

Finally, the inventors surprisingly observed that the capsules according to the invention comprise neuronal cells having a more mature phenotype than those included in the capsules based on Matrigel® (outside the invention). These results are presented in FIG. 9. The inventors analysed the expression of certain genes present in the cell population of the neural tissue at D24 cultured in the capsules of the invention and the capsules based on Matrigel®. A positive control based on the addition of dopaminergic neuron progenitors into capsules was also added. The results show that the neural tissue present in the capsules of the invention has a profile close to that of the positive control, demonstrating the presence of a more mature phenotype.

Thus, the results clearly demonstrate that a fibrin mesh is particularly suitable as substitute for the non-GMP extracellular matrix in the context of three-dimensional culture in cellular microcompartments.

Example 6—Large-Scale Production of Capsules According to the Invention

The aim of this study was to demonstrate that the capsule according to the invention is also suitable for use on a large scale, to be used in clinical, because requiring large quantities of cells, and consequently capsules producing them.

Protocol

The protocol is identical to protocol of example 4, with the difference that a 20 mg/ml fibrinogen solution is used, so as to obtain a cell density of the order of 0.85M/ml. Finally, the concentration of the thrombin solution is 0.04 U/ml.

Three conditions were studied in this study: culture in a 2D flask, culture in a small-scale bioreactor (30 mL) and culture in a large-scale bioreactor (500 mL).

Results

From D1 to D5 after encapsulation, the capsules were visually checked. At D7, cell appearance, viability, pluripotency and amplification factor are observed. The results are presented in Table 1 below.

TABLE 1

|  | Amplification | Viability (FACS) | Cysts at D 7 | Pluripotency (Oct4/Nanog) |
|---|---|---|---|---|
| Large Scale | x155 | 98.6 | No | 97.4% |
| Small Scale | x251 | 97.9 | No | 90% |
| Flask | x191 | 98.9 | No | 95.8% |

The results demonstrate that using fibrin as an extracellular matrix solves the technical problem of the present invention, including in large-scale culture in suitable bioreactors. Therefore, said capsules according to the invention are particularly suitable for use in clinical applications.

We claim:

1. A cellular microcompartment comprising:
   at least one layer of cells,
   an outer layer of hydrogel, and
   a fibrin mesh arranged between the outer layer of hydrogel and said layer of cells.

2. The cellular microcompartment of claim 1, wherein the fibrin mesh is entangled with the outer layer of hydrogel.

3. The cellular microcompartment of claim 1, wherein the outer layer comprises alginate.

4. The cellular microcompartment of claim 1, wherein the cellular microcompartment is closed.

5. The cellular microcompartment of claim 1, wherein the cellular microcompartment is a three-dimensional micro-compartment.

6. The cellular microcompartment of claim 1, wherein the cellular microcompartment has the shape of an ovoid, a cylinder, a spheroid, a sphere or a teardrop.

7. The cellular microcompartment of claim 1, wherein the one or more layer of cells comprises one or more of the following cells: eukaryotic cells, pluripotent cells, and/or differentiated cells.

8. The cellular microcompartment of claim 1, wherein the cellular microcompartment comprises a lumen.

9. The cellular microcompartment of claim 8, wherein the layer of cells, the fibrin mesh and the outer layer are successively organised around the lumen.

10. The cellular microcompartment of claim 1, wherein the fibrin is obtained from polymerisation of fibrinogen by thrombin during encapsulation and/or after encapsulation.

11. A set of two or more microcompartments, wherein at least one microcompartment in the set is the microcompart-ment of claim 1.

12. A medicament comprising the microcompartment of claim 1.

13. A method for preparing the cellular microcompart-ment of claim 1, comprising the following steps:
   a. mixing cells, optionally previously incubated in a culture medium with a mixture of fibrinogen,
   b. encapsulating the mixture from step (a) in a hydrogel layer;
   c. culturing the capsules obtained in step (b) in a culture medium,
      optionally, culturing the capsules resulting from step (c) for at least 1 day, preferentially from 3 to 50 days, and optionally recovering the obtained cellular microcompartments, and
      wherein a thrombin solution is added during step (b) and/or (c).

14. The method according to claim 13, wherein step (b) comprises the following sub-steps:
   i. bringing the mixture of step (a) into contact with a solution of hydrogel to form at least one drop, and
   ii. collecting said at least one obtained drop in a calcium bath capable of stiffening the hydrogel solution to form the outer layer of each microcompartment, the inner part of each drop consisting of the mixture of step (a).

15. The method according to claim 14, wherein the thrombin solution is added during step i) or ii).

16. The method of claim 13, wherein step i) consists of bringing the mixture of step a), the hydrogel solution, and an intermediate solution comprising said thrombin solution into contact.

17. The method of claim 13, wherein the thrombin solu-tion is added during step c).

18. The method of claim 13, wherein the concentration of fibrinogen is between 5 and 30 mg/mL, or 10-25 mg/mL.

19. The method of claim 18, wherein the concentration of fibrinogen is between 14 and 20 mg/mL.

20. The method of claim 13, wherein the concentration of the thrombin is between 0.001 and 2 U/mL, or between 0.01 U/mL and 0.03 U/mL.

21. The method of claim 13, wherein step b) is carried out by simultaneous co-injection of the hydrogel solution, of the mixture from step a) and optionally of said intermediate solution;
   said co-injection is carried out concentrically via a micro-fluidic or microfluidic injector forming a jet at the injector outlet consisting of the mixing of said solu-tions, said jet being divided into drops.

22. The method of claim 21, wherein the final opening diameter of the microfluidic injector is between 50 and 800 μm, preferentially between 80 and 240 μm, and the flow rate of each of the solutions is between 0.1 and 1000 mL/h, or between 10 and 150 mL/h.

23. A kit comprising a fibrinogen solution and a thrombin solution, wherein the kit is useful for preparing the cellular microcompartment of claim 1.

24. The kit of claim 23, wherein the fibrinogen solution and the thrombin solution are of human origin and are compliant with the regulations relating to Good Manufac-turing Practices (GMP).

* * * * *